United States Patent [19]

Gantzer

[11] 4,447,542
[45] May 8, 1984

[54] ANALYTICAL TEST COMPOSITION, DEVICE AND METHOD FOR THE DETERMINATION OF PEROXIDATIVELY ACTIVE SUBSTANCES

[75] Inventor: Mary L. Gantzer, Elkhart, Ind.

[73] Assignee: Miles Laboratories, Inc., Elkhart, Ind.

[21] Appl. No.: 481,630

[22] Filed: Apr. 4, 1983

[51] Int. Cl.$^3$ .................... G01N 33/52; G01N 33/72

[52] U.S. Cl. ........................... 436/66; 422/56; 427/2; 435/28; 436/904

[58] Field of Search .................. 436/66, 904; 422/56; 435/28; 427/2; 252/186.22, 186.26, 186.42

[56] References Cited

U.S. PATENT DOCUMENTS

| | | | |
|---|---|---|---|
| 3,012,976 | 12/1961 | Adams, Jr. et al. | 436/904 X |
| 3,252,762 | 5/1966 | Adams, Jr. et al. | 436/904 X |
| 4,372,746 | 2/1983 | Habenstein | 436/66 |
| 4,386,053 | 5/1983 | Motobayashi | 436/904 X |

FOREIGN PATENT DOCUMENTS 2906271  1/1981  Fed. Rep. of Germany ........ 435/28

*Primary Examiner*—Arnold Turk
*Attorney, Agent, or Firm*—Roger N. Coe

[57] ABSTRACT

A test composition, device and method for determining a peroxidatively active substance in a test sample, as well as a method for preparing the device, are disclosed. The composition comprises an organic hydroperoxide and an indicator capable of providing a detectable response in the presence of the organic hydroperoxide and peroxidatively active substance, wherein the organic hydroperoxide is a substituted cumene hydroperoxide having the formula:

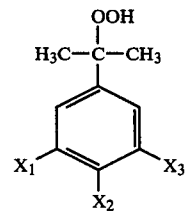

in which any one of the X substituents is lower alkyl of from 1 to 6 carbon atoms, Cl, Br, I, NO$_2$ or carboxyl; or any two of the X substituents, same or different, are lower alkyl of from 1 to 6 carbon atoms, Cl, Br, I, NO$_2$ or carboxyl. The device comprises a carrier matrix incorporated with the composition, and the method comprises contacting a test sample with the device and observing a detectable response in the device. A method for preparing the device comprises preparing a solution of the composition, wetting the carrier matrix therewith and drying the wetted matrix.

9 Claims, No Drawings

ANALYTICAL TEST COMPOSITION, DEVICE AND METHOD FOR THE DETERMINATION OF PEROXIDATIVELY ACTIVE SUBSTANCES

BACKGROUND OF THE INVENTION

1. Field of the Invention

This invention relates generally to analytical tests for the determination of peroxidatively active substances in test samples, and particularly to an improved test composition and device for such determinations having enhanced storage stability, as well as to a method for making and using the improved composition and device.

Many analytical methods are available for detecting the presence of peroxidatively active substances in biological samples such as urine, fecal suspensions and gastrointestinal contents. Hemoglobin and its derivatives are typical examples of such "peroxidatively active" substances because they behave in a manner similar to the enzyme peroxidase. Such substances have also been referred to as pseudoperoxidases, i.e., enzyme-like in that they catalyze the redox reaction between peroxides and such indicator compounds as benzidine, o-tolidine, 3,3',5,5'-tetramethylbenzidine, 2,7-diaminofluorene or similar substances, thereby producing a detectable response such as a color change. Most methods for determining the presence of occult blood in test samples therefore rely on this pseudoperoxidase activity.

2. Background Art

Analytical test methods have evolved over the years which rely on enzyme-like catalysis of the peroxidative oxidation of colorforming indicators. These include wet chemical or solution procedures and the so-called "dip-and-read" type, reagent-bearing strip devices. Of the former, a typical example is set forth in Richard M. Henry, et al., *Clinical Chemistry Principles and Techniques,* 2nd ed., (Hagerstown, Md.: Harper and Row, 1974), pp. 1124–1125. This procedure involves the use of glacial acetic acid (buffer), diphenylamine (indicator) and hydrogen peroxide. While such wet methods have proven analytical utility, they nevertheless have shortcomings, such as poor reagent stability and inadequate sensitivity.

Another method for the determination of peroxidatively active substances, and one presently preferred by most clinical assayists, employs the "dip-and-read", solid phase reagent strip device. Typical of such devices are those commercially available from the Ames Division of Miles Laboratories, Inc. under the trademark HEMASTIX®. They comprise, in essence, a porous paper matrix affixed to a plastic strip or handle. The matrix is impregnated with a buffered mixture of an organic hydroperoxide, for example, cumene hydroperoxide, and an indicator compound. Upon immersion in a liquid containing an analyte such as hemoglobin, myoglobin, erythrocytes or other pseudoperoxidases, a blue color develops in the matrix, the intensity of which is proportional to the concentration of the peroxidatively active substance in the sample. Thus, by comparing the color developed in the matrix to a standard color chart, the assayist can determine, on a semiquantitative basis, the amount of analyte present in the sample.

Reagent strips possess a number of advantages over wet chemistry methods, for example: greater ease of use because neither the preparation of reagents nor attendant apparatus is required; greater comparative stability of reagents because of the dry, solid reagent state, resulting in improved accuracy, sensitivity and economy. However, a serious disadvantage of many conventional, presently-available reagent strip test devices has been limited "shelf-life", i.e., a lack of storage stability over prolonged periods following manufacture, resulting in markedly decreased reactivity to the presence of peroxidatively active analytes when the devices are used. Thus, because analytical tools such as reagent strips usually are not used immediately after manufacture, but stored for varying periods of time before use, and because too long a period between manufacture and use of conventional reagent strips can result in a severe loss of reactivity, leading to false negative test results, enhanced shelf-life can be a marked asset: the better the shelf-life, the more dependable the analytical results.

Conventional solid phase reagent strip devices for determining peroxidatively active substances, e.g., occult blood or hemoglobin in urine, typically utilize as an indicator system the porphyrin-catalyzed oxidation of a benzidine-type indicator, for example, o-tolidine or 3,3',5,5'-tetramethylbenzidine, by an organic hydroperoxide, such as cumene hydroperoxide. Such conventional test strips, however, are known to be particularly prone to loss of reactivity during prolonged storage, or storage at elevated temperatures—a phenomenom which is believed to be due either to volatility or chemical degradation of one or more reagent ingredients of the strip. Not only have substantial losses of reactivity been observed in such conventional reagent strips following storage at ambient temperatures, but those losses appear to be substantially accentuated, and the rate of loss accelerated, by storage at elevated temperatures. Possible explanations for the losses of reactivity in reagent strips are: (1) key ingredient(s) of the reagent composition decompose or volatilize, so that the level of ingredient(s) falls below the minimum level necessary to maintain adequate reactivity; and (2) two or more ingredients in the strip interact deleteriously, producing one or more new species which are unreactive or inhibitory.

Attempts to stabilize the reactivity of reagent compositions, and solid phase strip devices made therefrom for determining peroxidatively active substances, have followed various lines of approach. For example, U.S. Pat. No. 3,092,463 to Adams, Jr. et al., discloses an improved test composition and device for detecting occult blood in body fluids. The composition comprises an organic hydroperoxide encapsulated or entrapped in microspherical bubbles of a colloid substance, an indicator or dye precursor capable of accepting transfer of oxygen from the organic hydroperoxide to produce a color response induced by the catalytic action of the prosthetic group of hemoglobin, and a buffer for maintaining the pH of the substance being tested within the range of from 4 to 6.5. This patent discloses that the colloid substance, for example, polyvinyl alcohol, gelatin, gum arabic or carboxy vinyl polymer, used to encapsulate or entrap the hydroperoxide, can provide stabilization of the reactivity of preferred embodiments of the test device produced from the composition even after 300 hours storage at 75° C., whereas similar devices prepared without encapsulation of the hydroperoxide lost reactivity after 24 hours at 50° C.

Other disclosures of stabilized test compositions and devices include the approach of U.S. Pat. No. 3,252,762 to Adams, Jr. et al., wherein the organic hydroperoxide used is encapsulated in a colloidal material such as gelatin which is hardened by fixing with a dialdehyde polysaccharide. Such compositions, containing a hydroperoxide so encapsulated, a suitable indicator and a buffer, are said to exhibit enhanced stability under various adverse temperature conditions, Still further disclosed attempts at stabilization of such reagent strip devices include a recitation in *Chemical Abstracts,* Vol. 85, p. 186 (1976), describing a two-dip method for preparing reagent strips containing o-tolidine and phenylisopropyl hydroperoxide. This disclosure reports making a solution of the indicator (o-tolidine.2HCl) and polyvinylpyrrolidone in ethanol. To this solution was added a small amount of surfactant and enough citrate buffer to provide a pH of 3.7, whereafter filter paper strips impregnated with ethyl cellulose were dipped in this solution and dried. The impregnated filter paper was subsequently dipped into a second solution containing 1,4-diazabicyclo [2,2,2]octane, phenylisopropyl hydroperoxide and polyvinyl pyrrolidone, dissolved in an ethanol-toluene mixture. The thrust of this work was to stabilize the peroxide and indicator combination through the use of the bicyclooctane derivative and the polyvinylpyrrolidone.

A similar method is disclosed in U.S. Pat. No. 3,853,471. This patent discloses the use of phosphoric or phosphonic acid amides where the substituent amido groups are primarily N-morpholine radicals.

Other approaches to stabilized reagent compositions include that of U.S. Pat. No. 4,071,317, wherein various diluent compounds, such as a mixture of dimethyl sulfone and N,N-dimethyl formamide, are employed along with cumene hydroperoxide and an indicator; of U.S. Pat. No. 4,071,318 (use of borate esters); and of U.S. Pat. No. 4,071,321 (use of both diluents and borate esters).

Another reference which is of interest to these general concepts is U.S. Pat. No. 3,236,850, directed toward stabilizing organic hydroperoxides used as catalysts and oxidizing agents. This reference discloses the use of primary, secondary or tertiary amine salts with organic peroxides, and is not directed to stability problems of solid phase reagent test strip devices.

Despite the inherent analytical advantages of solid phase reagent strip devices over wet chemistry procedures, and the foregoing exemplary advances in the art of stabilizing the reactivity of such strip devices, the stability characteristics of the latter, particularly in the case of devices for the determination of peroxidatively active substances, are in need of still further improvement. Whereas the properties of current solid phase, state-of-the-art compositions and devices for determining peroxidatively active substances are greatly enhanced over those of wet chemical methods, and over those of methods including no stability-enhancement techniques, it would nonetheless be greatly advantageous if even more stability during prolonged storage could be afforded, and more sensitivity to peroxidatively active analytes following such storage could be achieved, without the need for the addition of chemical substances, isolation of reagents by encapsulation, or similar relatively complicated and expensive treatments of such compositions and devices. For example, it would be a great advance in the art to provide suitable, direct substitutes for the well-known organic hydroperoxides which are conventionally used in solid phase test compositions and devices, substitutes which would render the reagent systems of these compositions and devices more stable during long-term storage.

Conventionally-used hydroperoxides include, for example, cumene hydroperoxide, t-butyl hydroperoxide, diisopropylbenzene hydroperoxide, 2,5-dimethylhexane-2,5-dihydroperoxide and paramenthane hydroperoxide. However, any suitable substitute for such compounds must not only be capable of participating similarly in the redox reaction with a peroxidatively active substance (analyte), in the presence of the conventional indicator systems used, to produce a detectable response such as a color change or change in the amount of light absorbed or reflected by the test composition, but also must exhibit such reactivity to an extent comparable to that of the conventional hydroperoxides typically used.

It has now been postulated that the frequently-observed losses of reactivity, leading to lack of storage stability or "shelf-life", of conventional solid phase reagent compositions and strip devices for determining peroxidatively active substances, may be attributable primarily to loss and/or chemical degradation of the organic hydroperoxide used in the reagent strip. Such loss or degradation could occur, for example, from decomposition or volatilization of the hydroperoxide or chemical interaction with other strip constituents. However, it is now believed that degradation due to decomposition or deleterious interaction may account for most reactivity losses. The mechanism causing such degradation is at the present unknown.

SUMMARY OF THE INVENTION

It has now been discovered, and the present invention is based upon this discovery, that present state-of-the-art conventional reagent systems for determining peroxidatively active substances can be improved substantially, and the aforementioned stability problems of such conventional systems largely overcome, through the advantageous inclusion of certain substituted cumene hydroperoxides in such reagent systems. According to the invention these substituted cumene hydroperoxides are used in place of the organic hydroperoxides commonly used in the art, resulting in enhanced economy and reliability over stabilized compositions employing such techniques as isolation of reagents, additives or the like.

Conventional reagent systems for determining peroxidatively active substances generally comprise an organic hydroperoxide and a redox indicator such as o-tolidine or 3,3',5,5'-tetramethylbenzidine. A peroxidatively active analyte, because it mimics the enzyme peroxidase, catalyzes or otherwise participates in a reaction between the indicator and organic hydroperoxide which yields a color, the intensity of which is indicative of the concentration of the analyte. Unlike such conventional analytical reagent systems, according to the present invention there is provided an improved analytical composition for determining peroxidatively active substances in a test sample. The composition comprises an organic hydroperoxide and an indicator capable of providing a detectable response in the presence of the organic hydroperoxide and the peroxidatively active substance, wherein the organic hydroperoxide is a substituted cumene hydroperoxide having the formula:

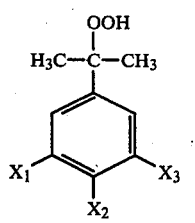

in which any one of the X substituents is lower alkyl of from 1 to 6 carbon atoms, Cl, Br, I, $NO_2$ or carboxyl; or any two of the X substituents, same or different, are lower alkyl of from 1 to 6 carbon atoms, Cl, Br, I, $NO_2$ or carboxyl. Preferred substituted cumene hydroperoxides are p-chlorocumene hydroperoxide and p-bromocumene hydroperoxide; most preferred is p-chlorocumene hydroperoxide.

The present invention also provides an improved analytical device for determining peroxidatively active substances. The device, in a preferred embodiment, comprises a carrier matrix incorporated with the improved composition of the invention. It is believed that the overall effect of the combination of the substituted cumene hydroperoxide in the composition with the other, largely conventional ingredients used therein enables the reactivity of the composition to be significantly stabilized, particularly over long periods of storage at both ambient and elevated temperatures, and provides advantageously enhanced "shelf-life", by comparison with conventional compositions and devices, as well as excellent sensitivity to the presence of a peroxidatively active analyte in a test sample. Thus, in terms of functionality as an oxidizing agent in the composition, enabling the accurate detection of such analytes, the substituted cumene hydroperoxides of the invention have been found to exhibit characteristics substantially identical to known hydroperoxides commonly used in the art for this purpose.

In addition, a method for using the analytical device of the invention is provided, as well as a method for making it. In a preferred embodiment, the device is used by immersing it into a liquid test sample under analysis, and observing the response, such as a color change, produced therein. Preferably, the method for making the device comprises incorporating a carrier matrix, for example a bibulous paper, with a solution or suspension of the ingredients of the composition.

DETAILED DESCRIPTION OF THE INVENTION

During development of the present invention, it was decided to attempt to overcome the aforedescribed stability problems of conventional reagent compositions and devices without resort to any heretofore known methodology. To this end, a series of substituted benzylic hydroperoxides were initially prepared by largely conventional organic chemistry procedures. The compounds which were synthesized reflected substituents on the aromatic ring hypothesized to possibly exert a stabilizing effect on the hydroperoxide functional group, it being presently believed that the destabilizing effect of electron withdrawing groups might overcome the problem of reagent instability if it is due to chemical decomposition or deleterious interaction of the hydroperoxide and other reagents.

Accordingly, the substituted cumene hydroperoxides which were determined to be suitable for use in the test composition and device of the instant invention include mono-and-di-substituted cumene hydroperoxides, and mixtures thereof, having the general structure:

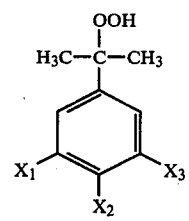

in which any one of the X substituents is lower alkyl of from 1 to 6 carbon atoms, Cl, Br, I, $NO_2$ or carboxyl; or in which any two of the X substituents, same or different, are lower alkyl of from 1 to 6 carbon atoms, Cl, Br, I, $NO_2$ or carboxyl. Thus, according to the present invention suitable substituted cumene hydroperoxides include, for example, p-chlorocumene hydroperoxide, p-bromocumene hydroperoxide, p-nitrocumene hydroperoxide, p-carboxycumene hydroperoxide, 3,4-dichlorocumene hydroperoxide, m-chlorocumene hydroperoxide, o-chlorocumene hydroperoxide, m-isopropylcumene hydroperoxide, o-methylcumene hydroperoxide, p-methylcumene hydroperoxide, as well as mixtures of these compounds in various proportions. Moreover, it is to be appreciated that all such compounds as defined structurally above are suitable for use in the present invention, although p-chlorocumene hydroperoxide and p-bromocumene hydroperoxide are presently preferred, p-chlorocumene hydroperoxide being most preferred. Thus, the selection of a particular substituted cumene hydroperoxide, or mixture of these compounds, is a matter of routine choice well within the capabilities of one of ordinary skill in the art, given the disclosure hereof.

The suitable substituted cumene hydroperoxides for use in the invention are either available commercially or can be readily prepared by the routineer from commercially available materials, using largely conventional organic synthesis techniques. For instance, substituted cumene hydroperoxides having p-chloro, p-bromo and 3,4-dichloro groups, as indicated in the Examples, infra, can be prepared from the corresponding acetophenones using procedures such as those described in A. Maerucker, Org. Reactions, 14, 270 (1965), S. Trippett, Quart. Rev. (London), 17, 406 (1963), C. Marvel, R. Allen and C. Overberger, J. Am. Chem. Soc., 68, 1088 (1946), and other well-known organic chemistry references. For example, reaction of p-chloroacetophenone with methylenetriphenylphosphorane, prepared from triphenylmethylphosphonium bromide and n-butyllithium/hexane in dry tetrahydrofuran at 0° C., produces, after purification by filtration, solvent removal, and distillation at reduced pressure, p-chloro-α-methylstyrene. Hydrogenation of the disubstituted double bond without hydrogenolysis of the chlorine substituent can be then effected using platinum oxide in ethanol. Purification by filtration, solvent removal, and distillation under reduced pressure, produce p-chlorocumene hydroperoxide. Substantially identical, largely conventional routes can be followed to prepare the p-bromo- and 3,4-dichlorocumene hydroperoxide forms, for example, as well as other mono- and di-substituted cumene hydroperoxides suitable for use in the present invention.

The amount of substituted cumene hydroperoxide used in the composition and device of the invention is not of critical importance, and is a matter of routine choice for one skilled in the art. Thus, for example, one would choose a sufficient amount which would enable the chemical interactions and changes necessary so as to render the composition or device reactive to the presence of a peroxidatively active analyte to an extent desired in a particular analytical situation, depending on such factors as whether the analytical test (assay) is designed for screening or for semiquantitative or quantitative determination of the analyte. Thus, such amount can be substantially the same as the amount of conventional hydroperoxides, such as cumene hydroperoxide, used in heretofore known semiquantitative formulations, such as, for example, those of U.S. Pat. Nos. 3,092,976, 3,092,463 and other similar disclosures, to which reference can be made for preferred hydroperoxide concentration ranges. It is thus to be appreciated that direct, selective quantitative replacement of known hydroperoxides in conventional formulations can be made in the composition and device of the invention to achieve the advantages heretofore described, without materially affecting the functionality and sensitivity of the assay in any given case.

As previously indicated, the test composition of the invention which is improved by a suitable substituted cumene hydroperoxide contains at least, in addition, an indicator compound which is capable, in the presence of the substituted cumene hydroperoxide and a peroxidatively active substance, of producing a detectable response, such as a color change or other response detectable visually or by instrumental means. Suitable indicators can comprise the so-called "benzidine-type" compounds, for example, benzidine, o-tolidine, 3,3',5,5'-tetra(lower alkyl)benzidine, 2,7-diaminofluorene or mixtures of these substances in various proportions. By "lower alkyl" is meant an alkyl radical having 1 to 6 carbon atoms, including methyl, ethyl, n-propyl and isopropyl, and the various butyl, pentyl and hexyl isomers. Other suitable indicators include o-toluidine, p-toluidine, o-phenylenediamine, N,N'-dimethyl-p-phenylenediamine, N,N'-diethyl-p-phenylenediamine, p-anisidine, dianisidine, o-cresol, m-cresol, p-cresol, alpha-naphthol, beta-naphthol, catechol, guaiacol, pyrogallol or those of the heterocyclic azine series, for example, bis-(N-ethyl-quinol-2-one)-azine or (N-methylbenzthiazol-2-one)-(1-ethyl-3-phenyl-5-methtriazol-2-one)-azine. However, most preferred as an indicator is 3,3',5,5'-tetramethylbenzidine.

In a preferred embodiment, the improved test composition of the invention is incorporated on or with a carrier matrix to form a solid phase, "dip-and-read" test device. Such a test device of the invention can be prepared by various well known methods, which include impregnating an absorbent matrix material with a solution or solutions of the test composition and thereafter drying the impregnated matrix, thus incorporating within the matrix a finely divided, intimate mixture of the composition ingredients. Suitable carrier matrices which can be used include paper, cellulose, wood, synthetic resin fleeces, glass fiber paper, polypropylene felt, nonwoven or woven fabrics and the like. Most suitable and preferred for use in the present invention as a carrier matrix is a bibulous paper such as filter paper. It is to be appreciated, however, that selection of an appropriate material for use as a carrier matrix is a matter of routine choice for one skilled in the art, and that the matrix can take on various physical forms, all of which are intended as being within the scope of the present invention. The most preferred mode of preparation of the device is to impregnate the matrix in a one-step process wherein the ingredients of the composition are mixed together in a solution or suspension and the matrix is immersed, or dipped, into the solution, and thereafter removed and dried. The dried, impregnated matrix can then be affixed, by suitable means such as double-sided adhesive tape, to one end of a carrier member comprising, for example, an oblong plastic strip, the other end of the strip serving as a handle for ease of use.

In addition to the previously-described test composition ingredients which actively participate in the test reaction, further ingredients such as solvents to suspend the indicator used, thickening agents, wetting agents, buffers, emulsifying agents and other well known adjuvants can also be included in the test composition and device of the present invention. Thus, for example, as thickening agents various materials such as gelatin, algin, carrageenin, casein, albumin, methyl cellulose, polyvinyl pyrrolidone and the like can be used. As a wetting agent, it is preferable to use sodium laurylsulfate, but any long chained organic sulfate or sulfonate, such as dioctyl sodium sulfosuccinate or sodium dodecylbenzene sulphonate can also be used. For the buffer systems, there can be used tartrate, phosphate, phthalate, citrate, acetate, or succinate buffers. Preferably, the composition is buffered to a pH value of from about 5.5 to 7.0. As emulsifying agents there can be used polyvinyl alcohol, gum arabic, carboxy vinyl polymers and the like. The organic solvents which are useful to suspend the indicator include most nonreactive, volatile solvents such as dimethylformamide, chloroform, ethylene dichloride, benzene, ethyl acetate and the like.

In use, the impregnated matrix of the test device can be immersed in a sample fluid or liquid suspension of the material to be tested and immediately withdrawn. In the presence of a peroxidatively active substance, contact of the test composition with the sample gives a positive, detectable response, e.g., a color reaction. The color response can then be compared with precalibrated color standards for an estimation of the quantitative amount of peroxidatively active substance contained in the sample. Intact peroxidatively active substances, such as intact red blood cells, may appear as dots or flecks of color on the otherwise uncolored matrix. Hemolyzed red blood cells may uniformly color the matrix. In addition to visual comparison, various instrumental techniques can also be used, increasing the accuracy of the test by obviating the subjective determination of color by the human eye.

It is to be appreciated that the device of the invention can also be used to determine peroxidatively active substances not only in liquids but in solid or semi-solid substances such as feces, gastrointestinal contents and the like. Thus, for example, a thin layer of the solid or semi-solid substance can be applied to the carrier matrix of the device and the detectable response, such as color change, observed in the matrix.

It has been found that the improved test composition and device of the invention are not only advantageous over conventional test compositions and devices in terms of enhanced stability, but are also highly sensitive. In a preferred embodiment, the instant test composition has been found capable of detecting hemoglobin in urine at a concentration as low as 0.015 milligram per deciliter (mg/dl), which corresponds to a blood dilution of 1:1,000,000. This high degree of sensitivity is an unexpected advantage, and is at least commensurate with the sensitivity of many conventional "state-of-the-art" tests for peroxidatively active substances.

As described above, the composition of the present invention can be incorporated with a suitable carrier matrix in a variety of ways to form a test device. For example, the ingredients can be dissolved or suspended in a mixture of water and a suitable organic solvent, such as dimethylformamide, acetone, ethanol, or mixtures thereof. Such a solution or suspension can then be used to impregnate a filter paper carrier matrix. The carrier matrix can be dipped into or coated with the composition, for example with a doctor blade, or can be incorporated with the composition as an ink wherein the reagents are printed onto the matrix.

The method presently preferred is to impregnate filter paper with a solution or suspension of the ingredients of the composition, the preferred solvents being distilled or deionized water and/or dimethylformamide (DMF). Such impregnation can be accomplished by dipping a piece of the filter paper into the solution or suspension and then drying the paper in an air oven. To complete the device the dried paper is then cut into a square measuring about 0.6 centimeter (cm) on a side, which is mounted on one end of a polystyrene film strip measuring about 0.6×10 cm. Mounting is accomplished through use of double-faced adhesive tape, such as that commercially available from the 3M Company.

Another method for making the device of the invention is one wherein an aqueous first solution of some of the ingredients of the composition is impregnated into the filter paper matrix, and then an organic second solution including the substituted cumene hydroperoxide and indicator is impregnated into the matrix. Thus, in this "two-dip" procedure, the filter paper is impregnated with the first solution, dried, reimpregnated with the second solution of the hydroperoxide and indicator, and dried a second time.

The most preferred method for making the device of the invention is to prepare a first aqueous solution of ingredients of the composition, comprising reagents (except for the hydroperoxide and indicator), buffers, wetting agents and the like, and then to prepare a second organic solution of the hydroperoxide and indicator reagents along with all remaining ingredients, followed by mixing of the two solutions, dipping of the filter paper in the mixture and drying. The device is then completed as previously described.

EXAMPLES

The following Examples are provided to further demonstrate the concepts and advantages of the present invention. The Examples are intended to be illustrative of how to make and use the invention, and are not to be interpreted as limiting its scope in any way. Moreover, although largely conventional organic synthesis procedures for substituted cumene hydroperoxide used in preferred embodiments of the invention are set forth in the Examples in detail, it will be appreciated that this is also only by way of illustration. One of ordinary skill in the art will be able to use various procedures for synthesizing such compounds, as well as other suitable substituted cumene hydroperoxides for use in the invention, considering the teachings hereof and those of the reference works previously described. All percentages expressed herein are by weight, unless otherwise indicated, and all reactions except hydrogenations and oxidations were conducted under an argon atmosphere.

Example I: Test composition and test devices incorporating p-chlorocumene hydroperoxide a. Synthesis of p-chloro-α-methylstyrene To a slurry of triphenylmethylphosphonium bromide (71.4 grams (g), 200 millimole (mmole)) in 500 milliliters (ml) dry tetrahydrofuran (THF) (distilled from sodium/benzophenone), were slowly added dropwise 129 ml (200 mmole) 1.55 molar (M) n-butyllithium in hexane. The reaction mixture was stirred for 30 minutes at $-10°$ C. whereafter a solution of 30.92 g (200 mmol) 4-chloroacetophenone in 100 ml dry THF was slowly added dropwise. The reaction mixture was then stirred for one hour at $-10°$ C., slowly warmed to ambient temperature (about 23° C.) and stirring continued overnight. The mixture was thereafter filtered and the solvent removed by distillation at atmospheric pressure. Distillation, using a water aspirator, yielded 16.5 g (54.2% yield) of p-chloro-α-methylstyrene, boiling point (bp) 82°–86° C.

b. Synthesis of p-chlorocumene

A mixture of p-chloro-α-methylstyrene (15.7 g, 204 mmole), 20 milligrams (mg) platinum oxide, and 20 ml absolute ethanol was shaken on a Paar Hydrogenator for about 8 hours, beginning with an initial hydrogen pressure of 42 pounds-per-square-inch (psi). During this procedure, an additional 14 psi of hydrogen were added to the Hydrogenator reservoir. The mixture was then filtered and the solvent removed by careful distillation at atmospheric pressure. The residual material resulting was distilled using a water aspirator vacuum to yield 12.69 g (74% yield) of p-chlorocumene (bp 69°–74° C.).

c. Synthesis of p-chlorocumene hydroperoxide

To a mixture of p-chlorocumene (36.90 g, 239 mmole), 285 mg (1 mmole) stearic acid, 2.56 g (24.1 mmole) sodium carbonate, and 190 ml distilled water at 85° C. were added 38 mg of benzoyl peroxide. Oxygen gas was then bubbled through the reaction mixture for 48 hours, the reaction mixture was cooled, 150 ml water added, and the products extracted with three 100 ml portions of pentane. The organic extracts were filtered and the solvent removed in vacuo. The concentrated material was carefully added to 75 ml cold (25 percent) sodium hydroxide solution and allowed to stand for two hours. The material was then filtered through a precooled filter, and the solids were washed with three 50 ml portions of pentane. The filter cake was dried in vacuo, suspended in water, and carbon dioxide bubbled through the mixture until a pH value of 8 was obtained. The mixture was then extracted with three 100 ml portions of pentane and the solvent removed in vacuo. Recrystallization of the material from pentane yielded 1.52 g (2.9% yield) of p-chlorocumene hydroperoxide, melting point (mp) 32°–33.5° C. Iodometric titration of the product showed the material to be approximately 98 percent pure p-chlorocumene hydroperoxide.

d. Preparation of the test composition and test devices

A first solution was prepared by combining the following ingredients in the order listed:

25 ml distilled water
1.07 g sodium citrate
1.39 g citric acid Buffer; 0.1 Molar (M)* pH 6.9
3.34 g triethanolamine borate; 0.4 M*
0.5 g sodium laurylsulfate; 1.0%*
0.034 g ethylenediaminetetracetic acid A second solution was then prepared by combining the following:

25 ml dimethylformamide
0.2 ml 6-methoxyquinoline; 0.4%*
1.87 g p-chlorocumene hydroperoxide (prepared as previously described)
0.3 g 3,3′,5,5′-tetramethylbenzidine; 0.03 M*
0.05 g orange G dye

*Final concentration of ingredient in a mixed solutions.

The first solution was thoroughly mixed with the second solution to produce a test composition according to the invention having approximately a 0.2 M concentration of p-chlorocumene hydroperoxide.

To prepare a test device from the foregoing composition, a sheet of laboratory filter paper (Whatman 3MM) was impregnated with the composition by immersing it in the mixed solutions, removing the paper and drying in an air oven at 105° C. for about 8 minutes. A 0.6 centimeter (cm) square of the dried, impregnated paper was then cut and applied to one end of a polystyrene film strip, measuring about 0.6×10 cm, using a piece of double-sided adhesive tape (3M Company).

Testing of devices of the invention produced as described above in urine samples containing various concentrations of hemoglobin yielded visually discernible color levels semiquantitatively corresponding to the hemoglobin concentrations.

Example II: Test composition and test devices incorporating p-bromocumene hydroperoxide a. Synthesis of p-bromo-α-methylstyrene To a slurry of triphenylmethylphosphonium bromide (71.4 g, 200 mmole), in 500 ml dry THF at 0° C., were slowly added dropwise 135 ml (200 mmole) 1.44 M n-butyllithium in hexane. The mixture was stirred 30 minutes at 0° C., and a solution of 39.8 g (200 mmole) p-bromoacetophenone, in 100 ml dry THF, was slowly added dropwise. The mixture was allowed to warm slowly to ambient temperature, whereafter stirring was continued overnight. The stirred mixture was next filtered and the solvent removed by careful distillation at atmospheric pressure, the resulting residue was diluted with hexane, filtered, and the hexane removed by distillation. The remaining material was distilled, using a water aspirator vacuum, to produce 23.2 g (58.3% yield) of p-bromo-α-methylstyrene, bp 95°–98° C.

b. Synthesis of p-bromocumene

A 23.2 g quantity of p-bromo-α-methylstyrene (118 mmole), approximately 100 mg platinum oxide, and 150 ml absolute ethanol were shaken on a Paar Hydrogenator for four hours, beginning with an initial hydrogen pressure of 50 psi. The material was then filtered through a celite plug and the solvent removed by distillation at atmospheric pressure. The residue resulting was distilled using a water aspirator vacuum to produce 18.9 g (80.4% yield) of p-bromocumene, bp 88°–92° C.

c. Synthesis of p-bromocumene hydroperoxide

To a mixture of p-bromocumene (18.9 g, 95 mmole), 115.8 mg (0.408 mmole) stearic acid, 1.04 g (10.8 mmole) sodium carbonate, and 80 ml distilled water at 84° C. were added 15 mg of benzoyl peroxide. Oxygen was bubbled through the reaction mixture for 48 hours, whereafter the mixture was cooled, diluted with 150 ml water, and the products extracted with three 100 ml portions of pentane. The combined organic extracts were filtered through a celite plug and the solvent removed in vacuo. The concentrated material was carefully added to 25 ml of cold sodium hydroxide (25%) solution, allowed to stand for two hours, and then filtered through a pre-cooled filter. The filter cake was washed with pentane, and the washed solid material was suspended in water. Carbon dioxide was then bubbled through the solution until a pH of 8 was obtained. The mixture was next extracted with four 50 ml portions of pentane and the solvent removed in vacuo. Recrystallization from pentane yielded 1.31 g (5.95%) of p-bromocumene hydroperoxide, mp. 42°–42.5° C. Iodometric titration showed the product to be substantially pure p-bromocumene hydroperoxide.

d. Preparation of test composition and test devices

A test composition was produced according to the invention substantially as described in Example I, supra, with the exception that p-bromocumene hydroperoxide (1.38 g), prepared as described above, was used in place of p-chlorocumene hydroperoxide to produce a composition approximately 0.2 M in p-bromocumene hydroperoxide. The method of making the test devices from the composition was substantially as described in Example I, and testing of the devices was carried out, also as previously described, in urine samples containing various concentrations of hemoglobin. As in Example I, the testing yielded visually discernible color levels corresponding to the concentration levels of hemoglobin in the samples.

Example III: Test composition and test devices incorporating p-nitrocumene hydroperoxide a. Synthesis of p-nitro-α-bromocumene To a solution of 6.6 g, 40 mmole p-nitrocumene (obtained from Columbia Chemicals) in 70 ml carbon tetrachloride were added 6.83 g (44 mole) N-bromosuccinimide and 40 mg 2,2′-azobis-(2-methylpropionitrile). The mixture was refluxed for 4 hours and thereafter cooled, filtered and the solvent removed in vacuo to produce 8.4 g (87.2% yield) of p-nitro-α-bromocumene.

b. Synthesis of p-nitrocumene hydroperoxide

To a mixture of p-nitro-α-bromocumene (2.43 g, 10 mmole) in 10 ml dry ether, and 4 ml of 90% hydrogen peroxide cooled to 0° C., was added dropwise a solution of 2.40 g (10 mmole) silver trifluoroacetate in 20 ml dry ether. The reaction mixture was stirred at 0° C. for 30 minutes, filtered through a celite plug, and the filtrate washed with four 50 ml portions of water. The solvent was removed in vacuo and, upon cooling to −70° C., 1.59 g (80.8% yield) of p-nitrocumene hydroperoxide solidified. Iodometric titration showed the product to be about 96% pure.

c. Preparation of test composition and test device

A test composition was produced according to the invention substantially as described in Example I, supra, with the exception that p-nitrocumene hydroperoxide (1.23 g), prepared as described above, was used in place of p-chlorocumene hydroperoxide, to produce a composition approximately 0.2 M in p-nitrocumene hydroperoxide. The method of making the test devices from the composition was substantially as described in Example I, and testing of the devices was carried out, also as previously described, in urine samples containing various concentrations of hemoglobin. As in Example I, the testing yielded visually discernible color levels corresponding to the concentration levels of hemoglobin in the samples.

Example IV: Test composition and test devices incorporating 3,4-dichlorocumene hydroperoxide a. Synthesis of 3,4-dichloro-α-methylstyrene To a slurry of triphenylmethylphosphonium bromide (71.4 g, 200 mmole), in 500 ml dry THF at 0° C., were slowly added dropwise 135 ml (200 mmole) 1.44 M n-butyllithium in hexane. The reaction mixture was stirred for one hour at 0° C., whereafter a solution of 37.8 g (200 mmole) 3,4-dichloroacetophenone, in 100 ml dry THF, was slowly added dropwise. The mixture was then stirred overnight, while it was slowly warmed to ambient temperature. The resulting reaction mixture was filtered at ambient temperature and the solvent removed by distillation at atmospheric pressure. The resulting residue was distilled at reduced pressure (approximately 10 mm Hg), to produce 21.9 (58.8% yield) of 3,4-dichloro-α-methylstyrene, bp 97°–102° C.

b. Synthesis of 3,4-dichlorocumene 3,4-dichloro-α-methylstyrene (21.9 g, 118 mmole), approximately 100 mg platinum oxide, and 125 ml absolute ethanol were shaken on a Paar Hydrogenator for four hours, at an initial hydrogen pressure of 50 psi. The material was then filtered through celite, and the solvent removed by distillation at atmospheric pressure. The resulting residual material was distilled at reduced pressure to produce 19.9 g (95% yield) of 3,4-dichlorocumene, bp 123°–126° C.

c. Synthesis of 3,4-dichloro-α-bromocumene

A solution of 3,4-dichlorocumene (1.89 g, 10 mmole), N-bromosuccinimide (1.95 g, 11 mmole), approximately 40 mg, 2,2'-azobis(2-methylpropionitrile), and 50 ml carbon tetrachloride was refluxed for four hours, then allowed to stand overnight. The mixture was filtered through celite and the solvent removed in vacuo. Pentane (50 ml) was added to the residue along with activated charcoal and the material again filtered through celite. The solvent was removed in vacuo to produce 2.28 g (85.5% yield) of 3,4-dichloro-α-bromocumene.

d. Synthesis of 3,4-dichlorocumene hydroperoxide

To a mixture of 3,4-dichloro-α-bromocumene (2.28 g, 8.55 mmole), 3.5 ml 90% hydrogen peroxide and 15 ml dry ether at 0° C. was added dropwise a solution of 2.05 g (8.55 mmole) silver trifluoroacetate in 10 ml ether. The reaction mixture was stirred for about 30 minutes at 0° C. and then filtered through celite. The filtrate was next washed with four 50 ml portions of water, two 50 ml portions of saturated sodium bicarbonate, and again with 50 ml of water. The solvent was then removed, in vacuo, to produce 1.50 g (68% yield) of 3,4-dichlorocumene hydroperoxide. Iodometric titration showed the product to be 90.5% pure 3,4-dichorocumene hydroperoxide.

e. Preparation of test composition and device

A test composition was produced according to the invention substantially as described in Example I, supra, with the exception that 3,4-dichlorocumene hydroperoxide (1.46 g), prepared as described above, was used in place of p-chlorocumene hydroperoxide, to produce a composition approximately 0.2 M in 3,4-dichlorocumene hydroperoxide. The method of making the test devices from the composition was substantially as described in Example I, and testing of the devices was carried out, also as previously described, in urine samples containing various concentrations of hemoglobin. As in Example I, the testing yielded visually discernible color levels corresponding to the concentration levels of hemoglobin in the samples.

STABILITY TESTING

A series of experiments was conducted to determine the storage stability, i.e., "shelf-life" under ambient and elevated temperature conditions, of test devices which had been produced according to the invention as described in the Examples, supra.

A test composition, and devices produced therefrom in accordance with the invention, were prepared as described in Example I and, in addition, control devices were prepared which were substantially identical to the Example I devices, but which contained cumene hydroperoxide (2 ml, 0.2 M) rather than p-chlorocumene hydroperoxide. Following preparation, the devices were "stressed" by storage for one week in air ovens at 50° C. and 70° C. Storage for one week at 70° C. was considered to correspond to storage for approximately one year at ambient temperature. A set of the "stressed" strips was then dipped in urine samples known to be negative in peroxidatively active substances, and another set was dipped in urine samples to which had been added various amounts of human whole blood. The results of visual testing of the devices for color formation (i.e., ability to detect hemoglobin in the urine samples) are set forth in the following table. The visual color readings of the devices were assigned standard solution designations (SSD) which corresponded to a color chart containing color blocks corresponding to colors produced by reaction of a conventional hemoglobin test device with urine samples containing the various amounts of blood. The devices were tested first immediately after preparation, at ambient temperature, and then after the aforementioned "stress" periods; the change, expressed in SSD units, for the devices tested in each sample was then calculated.

| VISUAL TEST RESULTS: Change in SSD after one week of storage at 50° C. and 70° C. | | | | | |
|---|---|---|---|---|---|
| Sample Hemoglobin Concentration (mg/dl) | 0 | 0.015 | 0.045 | 0.135 | 0.405 |
| Example I Devices 50° (p-chlorocumene 70° hydroperoxide) | 0 0 | 3 8 | 5 18 | 3 10 | 2 12 |
| Control Devices 50° (cumene 70° hydroperoxide) | 0 0 | 2 10 | 5 20 | 5 20 | 5 25 |

Additional test devices which had been prepared in accordance with the invention as described in Example I, as well as control devices which contained cumene hydroperoxide rather than p-chlorocumene hydroperoxide, were tested as previously described in urine samples containing hemoglobin, except that color formation in the devices was monitored instrumentally using a device known as a Macbeth Colorimeter (commercially available from Kollmorgan Company). This device is a microprocessor-controlled, scanning reflectance spectrophotometer suitable for the rapid measurement of reflectance spectra in the visual range. Measurements of the performance of reagent strip test devices in the Macbeth Colorimeter enable the following advantages over visual observation of color formation in the same strips:

(1) the light source and the other conditions surrounding the sample remain fixed;

(2) the detector characteristics remain fixed, whereas with visual observation the detector (i.e., the eyes of the observer) can vary from person to person, and with the same person, from day to day;

and (3) instrumental measurement enables more precise quantitation of data than does visual observation and allows more objective comparisons to be made between results.

In order to meaningfully assess the data produced by the Macbeth Colorimeter, the results of the testing therewith were expressed in B* units. These units are an instrumental measure of the yellowness/blueness value in a three dimensional color space. In order to obtain a B* value from a given reflectance (color) value produced by the Macbeth Colorimeter, a correlation is made by using the procedure described in D. B. Judd and G. Wyszecki, *Color in Business, Science and Industry*, John Wiley & Sons, New York (1975). Thus, conventional test devices not in accordance with the invention and which are "unstressed", i.e., those considered substantially fully reactive, when immersed in urine samples containing 0.135 mg/dl hemoglobin visually produce a blue color; the corresponding correlated B* value is a small number (around 8). However, aged or otherwise "stressed" conventional devices, exhibiting a substantial loss of reactivity when dipped in urine containing 0.135 mg/dl hemoglobin, produce a green rather than blue color; such latter color correlates to a higher B* value (around 30). Accordingly, to determine the relative stability of test devices of the invention, the smaller the rate of change of B* with time under "stress" conditions, e.g., prolonged storage at elevated temperatures, the greater is the stability of the device.

Accordingly, Macbeth Colorimeter rate-of-change data was obtained from devices which had been produced according to the invention as described in Examples I-IV, supra, and from control devices which contained cumene hydroperoxide rather than the substituted cumene hydroperoxides of the devices of the invention. The devices were "stressed" by storage for one week at 70° C., and B* readings were obtained from the devices after immersion in urine samples containing 0.135 mg/dl hemoglobin immediately following their preparation as well as following that period of "stress". The rate-of-change of B* was then calculated. The average value of the rate-of-change of reactivity of the devices is set forth in the following table, in term of B* units per week.

| Device type | Rate-of-change (B*/week) |
|---|---|
| cumene hydroperoxide (control) | 24.86 |
| p-chlorocumene hydroperoxide (Ex. I) | 15.19 |
| p-bromocumene hydroperoxide (Ex. II) | 11.32 |
| p-nitrocumene hydroperoxide (Ex. III) | 15.54 |
| 3,4-dichlorocuemene hydroperoxide (Ex. IV) | 22.68 |

The foregoing instrumental data confirms that test devices of the invention which incorporated substituted cumene hydroperoxides exhibited substantially increased stability, under adverse storage and temperature "stress" conditions, by comparison with conventional devices which incorporated cumene hydroperoxide. Moreover, the enhanced stability, i.e., "shelf-life" of the devices of the invention advantageously enabled them to detect the presence of hemoglobin even after such "stress", whereas the degradation of reactivity of the conventional control device was comparatively so rapid and substantial as to render it much less reactive to hemoglobin and thus less desirable in terms of "shelf-life".

It is to be appreciated that many modifications and variations of the preferred embodiments of the instant invention as set forth herein are possible without departing from the spirit and scope of the invention, and that any limitations upon such spirit and scope are intended to be imposed only by the following claims.

What is claimed is:

1. In a composition for the determination of a peroxidatively active substance in a test sample, the composition comprising an organic hydroperoxide and an indicator capable of providing a detectable response in the presence of said organic hydroperoxide and peroxidatively active substance, the improvement wherein said organic hydroperoxide is a substituted cumene hydroperoxide having the formula

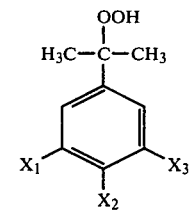

in which any one of the X substituents is lower alkyl of from 1 to 6 carbon atoms, Cl, Br, I, NO$_2$ or carboxyl; or any two of the X substituents, same or different, are lower alkyl of from 1 to 6 carbon atoms, Cl, Br, I, NO$_2$ or carboxyl.

2. The improved composition of claim 1 wherein the substituted cumene hydroperoxide is p-chlorocumene hydroperoxide.

3. The improved composition of claim 1 wherein the substituted cumene hydroperoxide is p-bromocumene hydroperoxide.

4. The improved composition of claim 1 wherein the substituted cumene hydroperoxide is selected from the group consisting of p-chlorocumene hydroperoxide, p-bromocumene hydroperoxide, p-nitrocumene hydroperoxide, p-carboxycumene hydroperoxide, 3,4-dichlorocumene hydroperoxide, m-chlorocumene hydroperoxide, o-chlorocumene hydroperoxide, m-isopropylcumene hydroperoxide, o-methylcumene hydroperoxide, p-methylcumene hydroperoxide and mixtures thereof.

5. The composition of claim 1 wherein the indicator comprises benzidine, o-tolidine, 3,3′,5,5′-tetra(lower alkyl)-benzidine, 2,7-diaminofluorene or mixtures thereof.

6. A test device for determining the presence of a peroxidatively active substance in a test sample comprising a carrier matrix incorporated with the improved composition of any one of claims 1 through 5.

7. A method for determining the presence of a peroxidatively active substance in a test sample, which method comprises the steps of contacting the sample with the device of claim 6 and observing a detectable response in the device.

8. A method for preparing a test device for determining the presence of a peroxidatively active substance in a test sample, comprising the steps of:
preparing a solution comprising the improved composition of claim 1;
incorporating the solution with a carrier matrix by wetting the matrix with the solution; and
drying the wetted matrix to leave a residue of the composition therein.

9. The method of claim 8, further comprising the additional step of affixing the dried matrix to a carrier member.

* * * * *